US009936690B2

(12) United States Patent
Benson

(10) Patent No.: US 9,936,690 B2
(45) Date of Patent: Apr. 10, 2018

(54) ULTRA-RAPID TISSUE CRYOPRESERVATION METHOD AND APPARATUS

(71) Applicant: BOARD OF TRUSTEES OF NORTHERN ILLINOIS UNIVERSITY, Dekalb, IL (US)

(72) Inventor: James Dale Benson, Dekalb, IL (US)

(73) Assignee: BOARD OF TRUSTEES OF NORTHERN ILLINOIS UNIVERSITY, Dekalb, IL (US)

(*) Notice: Subject to any disclaimer, the term of this patent is extended or adjusted under 35 U.S.C. 154(b) by 0 days.

(21) Appl. No.: 15/128,174

(22) PCT Filed: Mar. 27, 2015

(86) PCT No.: PCT/US2015/023014
§ 371 (c)(1),
(2) Date: Sep. 22, 2016

(87) PCT Pub. No.: WO2015/148935
PCT Pub. Date: Oct. 1, 2015

(65) Prior Publication Data
US 2017/0094962 A1  Apr. 6, 2017

Related U.S. Application Data

(60) Provisional application No. 61/971,979, filed on Mar. 28, 2014, provisional application No. 62/005,381, filed on May 30, 2014.

(51) Int. Cl.
A01N 1/00  (2006.01)
A01N 1/02  (2006.01)

(52) U.S. Cl.
CPC ......... *A01N 1/0257* (2013.01); *A01N 1/0221* (2013.01); *A01N 1/0284* (2013.01)

(58) Field of Classification Search
CPC ........................... A01N 1/0284; A01N 1/0257
See application file for complete search history.

(56) References Cited

U.S. PATENT DOCUMENTS 5,334,181 A    8/1994  Rubinsky et al.
5,628,197 A *  5/1997  Rada ................. F25D 3/10
                                                  269/21

(Continued)

FOREIGN PATENT DOCUMENTS

DE    10 2008048709    3/2010
DE    10 2011115467    4/2013

(Continued)

OTHER PUBLICATIONS

Search Report and Written Opinion issued in Int'l App. No. PCT/US2015/023014 (dated 2015).

(Continued)

*Primary Examiner* — Kara Johnson
(74) *Attorney, Agent, or Firm* — Barnes & Thornburg LLP; Alice O. Martin

(57) ABSTRACT

A method and apparatus for the processing of tissue and cellular material during cryopreservation and/or processing for microscopy. The method and apparatus maximizes heat transfer coefficients by using liquid-free cryopreservation protocols and maximizing glass transition characteristics through increasing pressure during cryopreservation. Cooling rates combined with megapascal pressures reduced the required concentration of cryoprotective agents (CPAs) needed for ice-free cell and tissue cryopreservation.

20 Claims, 8 Drawing Sheets

(56) References Cited

U.S. PATENT DOCUMENTS

| | | |
|---|---|---|
| 9,417,166 B2 | 8/2016 | Thorne et al. |
| 2008/0249350 A1 | 10/2008 | Marchitto et al. |
| 2009/0011505 A1 | 1/2009 | Leunissen |
| 2010/0281886 A1 | 11/2010 | Shaham et al. |
| 2014/0260346 A1 | 9/2014 | Fuhr et al. |
| 2016/0227762 A1 | 8/2016 | Van Sickle et al. |

FOREIGN PATENT DOCUMENTS

| | | | |
|---|---|---|---|
| WO | WO 2002/053967 | 7/2002 | |
| WO | WO 02053967 A1 * | 7/2002 | ............... F17C 3/08 |

OTHER PUBLICATIONS

Zhou et al., "Investigation on the thermal performance of a novel microchannel-aided device for vitrification of cells/tissues," *Applied Thermal Engineering*, 119: 189-196 (2017).

Supplementary Search Report issued in App. No. EP15768968 (dated Jan. 8, 2018).

* cited by examiner

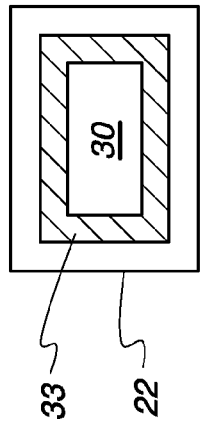
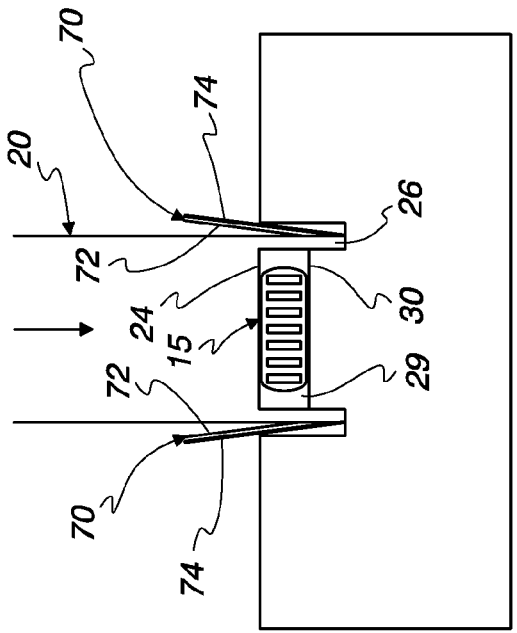
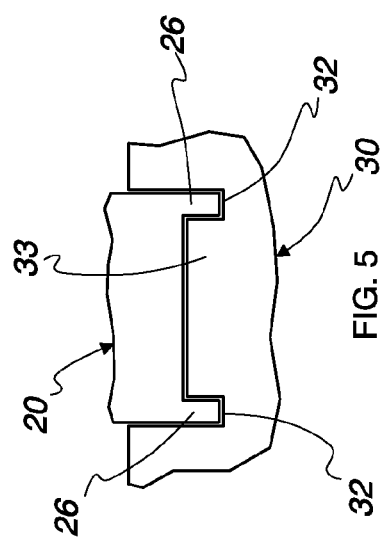
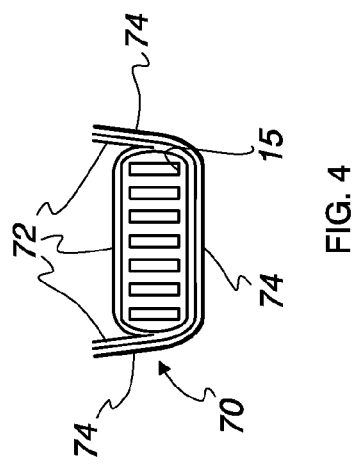

ULTRA-RAPID TISSUE CRYOPRESERVATION METHOD AND APPARATUS

CROSS REFERENCE TO RELATED APPLICATIONS

This application is a U.S. nationalization under 35 U.S.C. §371 of International Application No. PCT/US2015/023014, filed Mar. 27, 2015, which claims the benefit of priority under 35 U.S.C. § 119(e) to U.S. Provisional Patent Application No. 61/971,979, filed Mar. 28, 2014, and U.S. Provisional Patent Application No. 62/005,381, filed May 30, 2014. The disclosures set forth in the referenced applications are incorporated herein by reference in their entireties.

FIELD

The present disclosure relates to methods and apparatus for the processing of cells and tissues during cryopreservation and/or processing for microscopy.

BACKGROUND

The successful cryopreservation of tissues and other cellular material is of immense importance in a vast array of medical, agricultural, and scientific applications. There is a pressing need for reliable cryopreservation of many tissue types including articular cartilage, kidney, liver, and many more. Cryopreservation of these tissues would facilitate autologous donations for patients undergoing iatrogenic procedures, and would greatly facilitate banking, testing, and donor host matching for allogenic transplantation. For example, present methods do not routinely achieve more than about 5% recovery of human oocytes after cryopreservation and banking. The as-of-yet unachievable ability to cryopreserve human ovarian tissue would ameliorate this problem, as primordial follicles would be transplanted along with the rest of the ovarian tissue and mature oocytes could be collected as needed. Additionally, well cryopreserved tissues also pose considerable advantages over chemically preserved tissues for histological and pathological testing. In particular, they retain most biological functions and as such provide an additional avenue for functional as well as histological testing.

Conventional methods yield very limited recovery after thawing for most tissue types. This limited recovery is due, in part, to the maximal cooling and warming rates achievable by the cryopreservation method or system. Low cooling and warming rates allow for the formation of intra- and inter-cellular ice crystals that is widely believed to be irreversibly damaging to cells and tissues. This is ameliorated in part by the addition of chemical protectants, but the concentrations needed to allow for ice-avoidance at low cooling rates can be toxic to cells and tissues.

Currently, for tissues cryopreserved within secondary containers (e.g., sealed tubes) cooling and warming rates are severely limited by the heat transfer through multiple layers of tissue, media, tube and extra-tube cooling media (typically liquid nitrogen). Tissues cryopreserved in the absence of secondary containers (typically those plunged directly into liquid nitrogen) still have severely sub-optimal cooling and warming rates because heat transfer is limited by the Leidenfrost effect during cooling where nitrogen vapor formed upon exposure to the tissue acts as a local insulator, dramatically reducing cooling kinetics. The Leidenfrost effect is the insulating effect of vaporized liquid that occurs when an object much warmer than a liquid's boiling temperature is rapidly placed in contact with the liquid. During warming, the Leidenfrost effect is not present, but heat transfer coefficients of media such as water or tissue culture media are relatively low.

In view of the prevalence of existing cold-block designs for use with cryo-electron microscopy, it would be desirable to maximize the thickness of undisturbed tissue.

Cold block type cooling apparatus are seldom used in tissue cryopreservation due to the one-sided cooling of present cooling block designs; i.e., only one face of the block is cooled, not both, and therefore only one side of the sample is contacted by the cooling block and cooled. Coupled with the perceived need for fluid-tight sealed cooling containers, cooling block designs have not commonly been pursued for whole tissue cryopreservation. Such designs have, however, been used for cryopreservation of near-surface features from tissues for histological and pathological study, using, for example, freeze substitution in conjunction with electron microscopy. These techniques are reported to be successful (i.e., performed with ice-free cryopreservation) at a depth of approximately 200-500 micrometers. Because most tissues of interest are considerably thicker, this limitation is unacceptable for many applications.

However, when similar rates of cooling are achieved from not one, but two sides of the sample, then a combined survival depth of up to about 1 millimeter may be achievable. This is well within the realm of usable tissue depths and success may further be achieved with well-planned pre-cool treatment with ice-preventing chemicals such as ethylene glycol or glycerol. In fact, limited survival in the presence of high concentrations of these chemicals (known as Cryoprotective Agents or CPAs) has been well documented for a number of tissue types. The limiting factor in survival is the interplay between toxicity due to exposure to high concentrations of CPAs and the need for higher cooling rates at low concentrations.

SUMMARY

In exemplary embodiments, an apparatus is provided comprising a first thermal block having a male sealing member extending therefrom; a second thermal block having a female sealing member formed therein matable with the male sealing member; a first force applying means for applying a force to the first thermal block so as to move the first thermal block and the second thermal block into proximity; and, a chamber for holding the sample, the chamber defined by the first and second thermal blocks and the male sealing member and the female sealing member when the male sealing member is either proximate to or received by the female sealing member.

In exemplary embodiments, a method is provided for cryopreserving a sample of tissue or cellular material, comprising (a) placing the sample between at least two sheets of thermally conductive material; (b) providing a first thermal block having a male sealing member and providing a second thermal block having a female sealing member; (c) urging the first and second blocks toward each other under pressure so that that the sample and at least a portion of the at least two sheets are contacted between the first and second sealing members so that the first and second sealing members crimp a portion of each sheet to form a fluid-tight sealed chamber having the sample disposed therein; (d) cooling at least a portion of the first and second thermal blocks to a desired temperature at a desired rate of cooling; (e) separating the first and second blocks; and, (f) removing the sample in the container.

Other features will become apparent upon reading the following detailed description of certain exemplary embodiments, when taken in conjunction with the appended claims.

BRIEF DESCRIPTION OF THE DRAWINGS

The drawings disclose exemplary embodiments in which like reference characters designate the same or similar parts throughout the figures of which:

FIG. 3 shows a side elevational view of a portion of the exemplary embodiment of the apparatus of FIG. 1 in which a sample has been pressed between the upper and lower platens of the thermal blocks.

FIG. 4 shows a side elevational view of one exemplary embodiment of a sample container formed of two sheets, with a sample contained therein.

FIG. 5 shows a side elevational cutaway view of a upper block and a lower block in abutting relationship and showing a chamber formed therebetween.

FIG. 6 shows a top plan view of a portion of a lower thermal block and illustrating a groove surrounding the platen.

DETAILED DESCRIPTION

Figure 1:
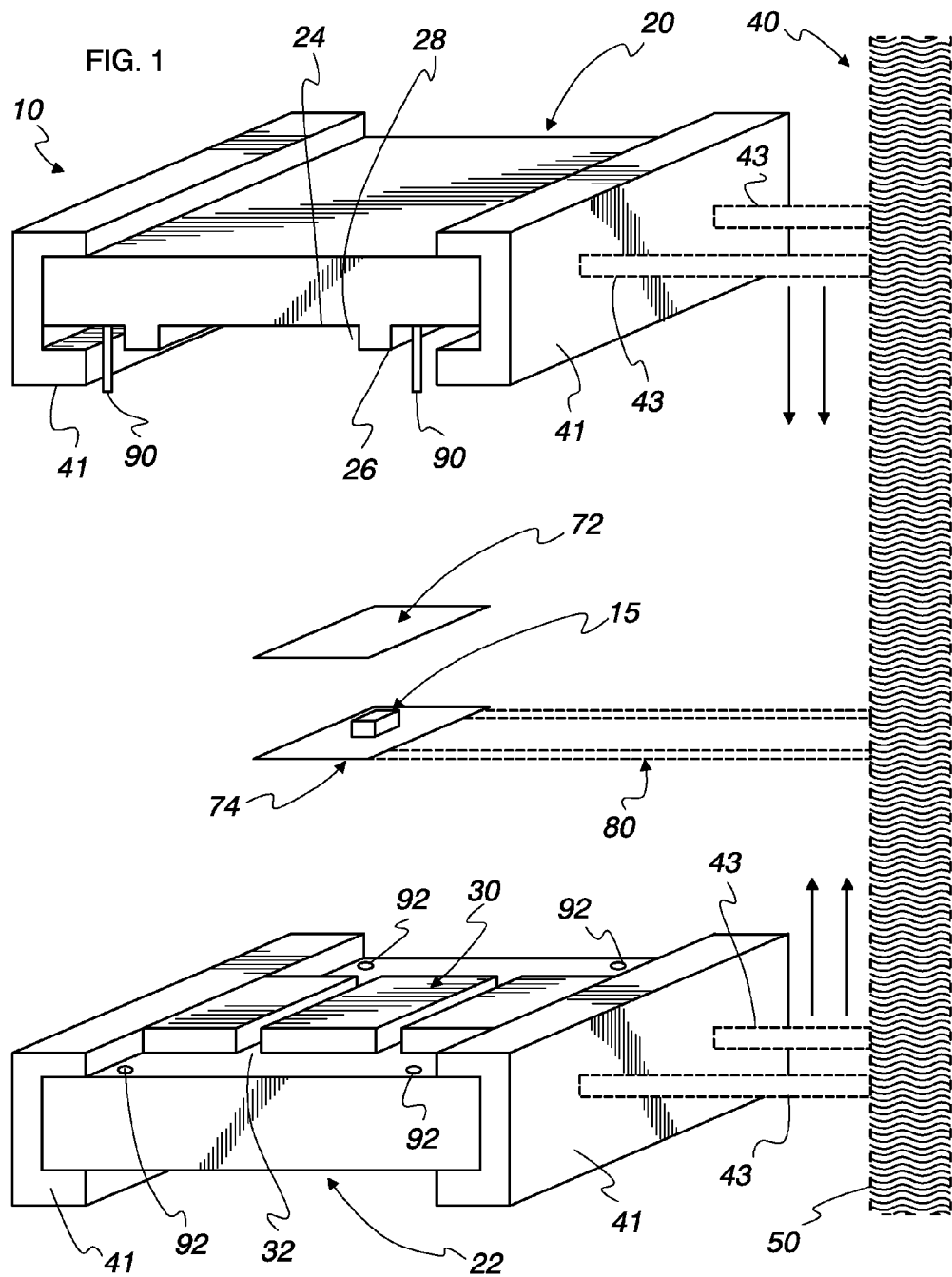
FIG. 1 shows a schematic perspective view of one exemplary embodiment of an apparatus including a press and thermal blocks (shown in partial cross-section) positioned above and below a sample and container.

Unless otherwise indicated, the drawings are intended to be read (for example, cross-hatching, arrangement of parts, proportion, degree, or the like) together with the specification, and are to be considered a portion of the entire written description of this invention. As used in the following description, the terms "horizontal", "vertical", "left", "right", "up" and "down", "upper" and "lower", as well as adjectival and adverbial derivatives thereof (for example, "horizontally", "upwardly", or the like), simply refer to the orientation of the illustrated structure as the particular drawing figure faces the reader. Similarly, the terms "inwardly" and "outwardly" generally refer to the orientation FIGS. 1-5 show an apparatus 10 according to a first exemplary embodiment for use in cryopreservation of a sample 15. The sample 15 may be tissue, single cells (such as, but not limited to, sperm, oocytes, stem, or the like), cellular material, or other organic material. An upper thermal block 20 and a lower thermal block 22 are made of a thermally conductive material, such as, but not limited to, metal. In exemplary embodiments, the thermal blocks 20, 22 may be made of, or contain, copper, aluminum or other metal, alloys, combinations thereof, or the like. The thermal blocks 20, 22 may be made of the same material, or each made of a different material. The upper block 20 has a platen 24 and male first sealing member. In exemplary embodiments, the platen 24 is generally flat. The first sealing member may be a rim 26 that extends outward from the platen 24 surface. Alternatively, the first sealing member may be a plurality of tabs or other protrusions extending from the platen 24 surface. The platen 24 and rim 26 form a recess portion 28 that is one part of a chamber 29 formed with the bottom block 22.

The lower block 22 has a platen 30 (a generally flat surface in various exemplary embodiments). In exemplary embodiments, a female second sealing member may be a groove 32 formed in the lower block 22. The groove 32 can receive the rim 26. In alternative exemplary embodiments, upper block 20 sealing member 26 may be a groove and the lower block sealing member may be a rim. Other sealing systems are possible, as well. In exemplary embodiments, the sample may be sealed in an appropriate container before use. A basic function of the first and second sealing members is to assist in creating a fluid-tight seal around the sample.

The groove 32 extends generally around at least a portion of the perimeter (but typically, around the entire perimeter) of platen 30. When the upper block 20 and lower block 22 are brought together, the rim 26 enters the groove 32. In exemplary embodiments, the rim 26 is deeper than the groove 32 so that when the blocks 20, 24 are in an abutting relationship there is a gap 33 formed between the platen 24 and the platen 30. The gap 33 is bounded on the sides by the rim 26 and a chamber 29 is formed in which the sample 15 can be held, as described in further detail hereinbelow. In exemplary embodiments, the rim 26 and groove 32 can be shaped to have a generally square or rectangular perimeter, as shown in FIG. 6. In alternative exemplary embodiments, the rim 26 and groove 32 can have a circular, elliptical or other regular or irregular shape. In an alternative exemplary embodiment, the lower platen 30 may be slightly concave curved, and the upper platen 24 may be slightly convex curved so as to provide as slight bowl shape to the container after sealing. A slight bowl-shaped container may also better match a sample 15 having a bottom side with a radius of curvature. In exemplary embodiments, the upper block 20 may be removably associated with an upper press 40, which includes a mechanism 44 (not shown) that can exert downward pressure on the upper thermal block 20 when actuated to urge the upper block 20 toward the lower block 22. In exemplary embodiments, the mechanism 44 may be designed using at least one variable hydraulic or pneumatic piston or ram, or at least one worm drive, screw, gear or other mechanisms known to those skilled in the art to allow the adjustment of the final distance between plates and minimal and/or maximal force applied to the sample between the platens 24, 30. The mechanism 44 may be associated with at least one motor or pump (not shown) as is known to those skilled in the art. Alternatively, the mechanism 44 may be an electrically activatable solenoid. Alternatively, the mechanism 44 may be a manual mechanism, such as a hand crank or lever connected to a gear which in turn is connected to a movable piston or rod. In exemplary embodiments, the upper block 20 can be coupled to, fitted on or in or otherwised attached or associated with the press 40. In one exemplary embodiment, the upper thermal block 20 and the lower thermal block 22 are operatively associated with the mechanism 44. In exemplary embodiments, at least one thermal block holder 41 may be associated with a portion (for example, a side) of the upper thermal block 20. Similarly, at least one thermal block holder 41 may be associated with the lower thermal block 22. In an alternative exemplary embodiment, one of the thermal blocks is fixed and the other is operatively associated with the mechanism 44 via at least one connecting member, such as a rod 43.

In exemplary embodiments, the lower block 22 may be fixed with respect to the upper block 20. In other exemplary embodiments, the lower block 22 may be removably associated with a second press 50 and a second press mechanism 52 (both not shown) that may be constructed in a manner similar to that as described with respect to the upper press 40. In exemplary embodiments, the first and second presses 40, 50 may be a single press with the ability to move both upper and lower blocks 20, 22 toward and away from each other.

In exemplary embodiments, a sample container 70 is constructed of a relatively thin upper sheet 72 and lower sheet 74 of material (as shown in, for example, FIG. 1). In exemplary embodiments, such material is thermally conductive. In exemplary embodiments, the material is made of metal. In exemplary embodiments, the metal may be aluminum. In exemplary embodiments, either or both sheets 72, 74 may be solid. In exemplary embodiments more than one upper sheet 72 and/or more than one lower sheet 74 may be included.

In exemplary embodiments, the sheets 72, 74 are wider and longer than the width and length across the platen 30 and groove 32. In exemplary embodiments, the sheets 72, 74 are constructed so that the edge area can be crimped, as described in greater detail hereinbelow, to form a sealed container 70 that can contain a sample 15, as shown in FIG. 4.

Figure 2:
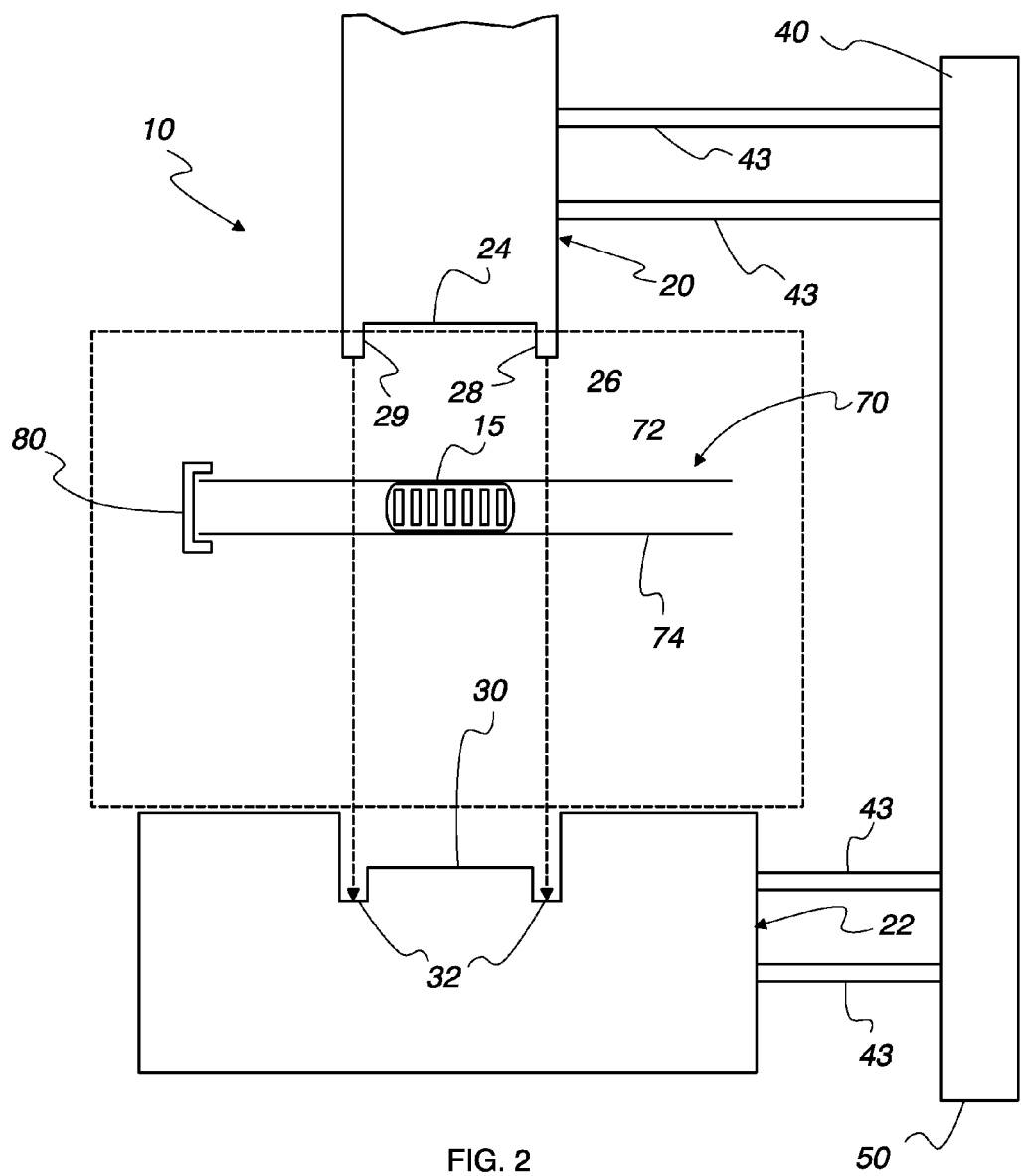
FIG. 2 shows a side elevational view of the apparatus of exemplary embodiment of FIG. 1.

In exemplary embodiments, a support 80 (as shown, for example, in FIG. 2) can support and suspend the sheets 72, 74 between the upper and lower blocks 20, 22. In exemplary embodiments, the support 80 may be associated with the upper block 20 or the lower block 22. Alternatively, the support 80 may be free standing and used to position the sheets 72, 74 and sample between the platens 24, 30, and then, optionally, removed. In exemplary embodiments, the sheets 72, 74 are associated with the support 80 such that the support 80 can be dissociated from the container 70 when the container 70 is formed. In exemplary embodiments, the support 80 may consist of one or more fingers 82 that extend from the frame of the press through the area between the thermal blocks 20, 22, as shown in FIG. 2. The finger(s) 82 can be placed at a distance apart so that they support the support 80. The support 80 and the thermal blocks 20, 22 can be constructed so that the support can fit between the thermal blocks in such a way so that the thermal blocks may close entirely around the sample 15 without being obstructed by the support 80. When the upper and lower blocks 20, 22 are brought together and the rim 26 fits in the groove 32, the chamber 29 is formed. In exemplary embodiments, the thermal blocks 20, 22 may be maintained in a closed relationship by any of a number of different closure mechanisms, such as, but not limited to, one or more, locks, pins, snaps, hooks, hook and loop fasteners, straps, or the like. In exemplary embodiments, the upper thermal block 20 may have one or more first registration devices 90 and the lower thermal block 22 may have one or more second registration devices 92. In exemplary embodiments, the registration devices may be pins 90 and holes 92 (as shown in FIG. 1), tabs, posts, notches, a tongue and groove system, or the like. The first and second registration devices 90, 92 may co-operate to ensure that the thermal blocks 20, 22 are aligned with each other when pressed together.

In exemplary embodiments, the sheets 72, 74 may be supported by the support 80 so that the sheets 72, 74 (with the sample 15 sandwiched therebetween) come into contact with the upper and lower platens 24, 30 (respectively) simultaneously or nearly simultaneously when the upper and lower platens approach each other. The pressing action causes the rim 26 to enter the groove 32, which pushes the edges of the sheets 72, 74 into the recesses 33, thereby crimping the sheets 72, 74 together and forming a fluid-tight seal around the edge. The pressure of the compressing force may be controlled by the user. The amount of applied pressure would depend on the sample. Some samples may be sensitive to pressure and thus the minimal pressure should be applied so that there is good thermal contact between thermal blocks 20, 22 and the sample 15 (via the container 70). Other samples may be less sensitive to pressure such that higher pressures can be used, which may produce a benefit from the crystallization suppression that occurs under high pressure. In "high pressure" cryomicroscopy applications a pressure of approximately 200 MPa ($2 \times 10^8$ Pa) is typically used with cooling rates of about 7000 K/sec.

The thermal blocks 20, 22 can be cooled by circulating a cryogenic material around or through the blocks, by pre-cooling the blocks in a freezer, or cryogenic gas or liquid before placing in the block holders 41. In exemplary embodiments, the thermal blocks 20, 22 are solid. In exemplary embodiments, either or both of the thermal blocks 20, 22 may have pores, ports, spaces, holes, recesses, channels or spaces formed therein to permit passage of cryogenic material in, through or around the thermal blocks. In exemplary embodiments, the cryogenic liquid may be a liquid, such as, but not limited to, liquid nitrogen. In exemplary embodiments, the cryogenic material may be a gas, such as, but not limited to, cold dry nitrogen gas. In exemplary embodiments, the cryogenic material may be a liquid infused with a gas, in configurations known as an oscillating heat pipe. In exemplary embodiments, the cryogenic material may be a mixture of two or more gases or two or more liquids. In exemplary embodiments, the cryogenic material may be a mixture of at least one gas and at least one liquid.

In one exemplary embodiment of a cryopreservation method, a sample 15 of tissue or cellular material is placed between upper and lower sheets 72, 74 of a thin metal, metallic or other thermally conductive material. The support 80 is manipulated to position the sample 15 and sheets 72, 74 between the plates 24, 30. Optionally, the support 80 may then be removed. In exemplary embodiments, the sample 15 may be pre-equilibrated with cryoprotectant material or solution before coolant is circulated and before the sheets 72, 74 are sealed and the container 70 formed. In one exemplary embodiment, a cryogenic material, such as liquid nitrogen, is circulated around at least a portion of the upper and lower presses 40, 50. In exemplary embodiments, the cryogenic material may be circulated in the region proximate to the lower platen 30 surface and the upper platen 24 surface. The thermal blocks 20, 22 are moved toward each other by the press 40 or presses 40, 50 such that the upper and lower sheets 72, 74, with the sample 15 held therebetween, are sandwiched in the chamber 29 between platens 24, 30 so that a portion of the upper and lower sheets 72, 74 proximate to their edges are crimped between the rim 26 and groove 32. This forms a fluid-tight seal between the upper and lower sheets 72, 74 and seals the sample 15 in the container 70 so that fluids or other material in the external environment do not come in contact with the sample 15. In exemplary embodiments, it is desirable for the platens 24, 30 to contact the sheets 72, 74 (and, effectively, the sample 15) simultaneously or nearly simultaneously. Such contact on both sides of the sample 15 may provide more even and faster temperature transition than single-sided or non-simultaneous cooling (or warming) of the sample 15.

The sample 15 and container 70 are held in place within the chamber 33 (with a portion of the crimped sheets 72, 74 remaining outside of the chamber 33 in exemplary embodiments) for a sufficient length of time so that the sample 15 reaches equilibrium temperature with the thermal blocks and held at approximately the temperature of the cooling material (such as, for example, LN).

In exemplary embodiments, for ovarian cortex tissue equilibrated with 20% 1,2 Propane-Diol or for a sample 15 composed of human corneas equilibrated with 10% 1,2 Propane-Diol, the cooling at the center of the tissues may be in a range of from about $10^3$ to about $5 \times 10^5$ K/min. In exemplary embodiments, the cooling may be done at a rate in a range of from about $5 \times 10^3$ to about $5 \times 10^4$ K/min.

In exemplary embodiments, the first and second presses 40, 50 are moved away from each other and the upper and lower blocks 20, 22 (both still in an abutting or proximate relationship) and the container 70 locked together, removed and transferred to liquid nitrogen or other cryogenic material for storage. In other exemplary embodiments, the upper and lower blocks 20, 22 can be separated and stored the container 70 and the sample 15 contained therein can be removed.

When warming of the sample 15 is desired, the sealed container 70 containing the sample 15 is placed in the chamber 33 between the upper and lower blocks 20, 22. In exemplary embodiments, a warming fluid may used, such as, but not limited to, water, air, oil or the like, which can be circulated around at least a portion of the thermal blocks 20, 22 so as to pre-warm the thermal blocks. In other exemplary embodiments, heating coils may be used to warm the thermal blocks 10, 22. It may also be possible to use embedded electromagnets, infrared laser energy, other thermal energy source, or the like. The thermal blocks 20, 22 are rapidly moved toward each other so that the container 70 is positioned to be between the upper platen 24 when formed by the thermal blocks.

The pre-warmed upper and lower thermal blocks 20, 22 are rapidly pressed toward the sheets 72, 74. Alternatively, warming can be achieved in a warm-water bath. The sample 15 is warmed to the desired temperature by heat conduction from the preheated thermal blocks 20, 22 (or the water bath) through the sealed container 70 and into the sample 15. In exemplary embodiments, for a sample 15 composed of a 1 mm×10 mm×5 mm section of human ovarian cortex and for a sample 15 composed of 0.6 mm by 12 mm diameter human cornea the warming may be done at a rate in a range of from about $10^4$ to about $5 \times 10^5$ degrees C. per minute. In exemplary embodiments, the warming may be done at a rate in a range of from about $5 \times 10^3$ to about $5 \times 10^4$ K/min. This range is dependent on several factors. There will be an order of magnitude or more difference in cooling/warming rate from the outside to the inside of a given tissue or cell sample. This cooling/warming rate may also be dramatically dependent on tissue thickness. For ovarian cortex of 1 mm thickness, the theoretical maximal center cooling and warming rates are on the order of $5 \times 10^4$ K/min. On the other hand, for human corneas, the theoretical maximal center cooling and warming rates are on the order of $10^5$ K/min.

In exemplary embodiments, the sample 15 may be placed in a heat conducting fluid before it is sealed in the container 70. In exemplary embodiments, a thermal paste, grease or other material, such as those used in the electronics industry to facilitate the removal of heat from computer chips. Such materials may be used to increase the thermal conductivity of the medium surrounding the tissue. In exemplary embodiments, at least one inert mineral oil may be used. In exemplary embodiments, at least one mineral oil containing diamond nanoparticles may be used, such material has 1-2 orders of magnitude higher thermal conductivity that that of water, and may provide an additional benefit of not facilitating crystallization in the media outside the tissue. An oil-diamone mixture may also have the benefit of having lower compressibility than water.

Figure 7:
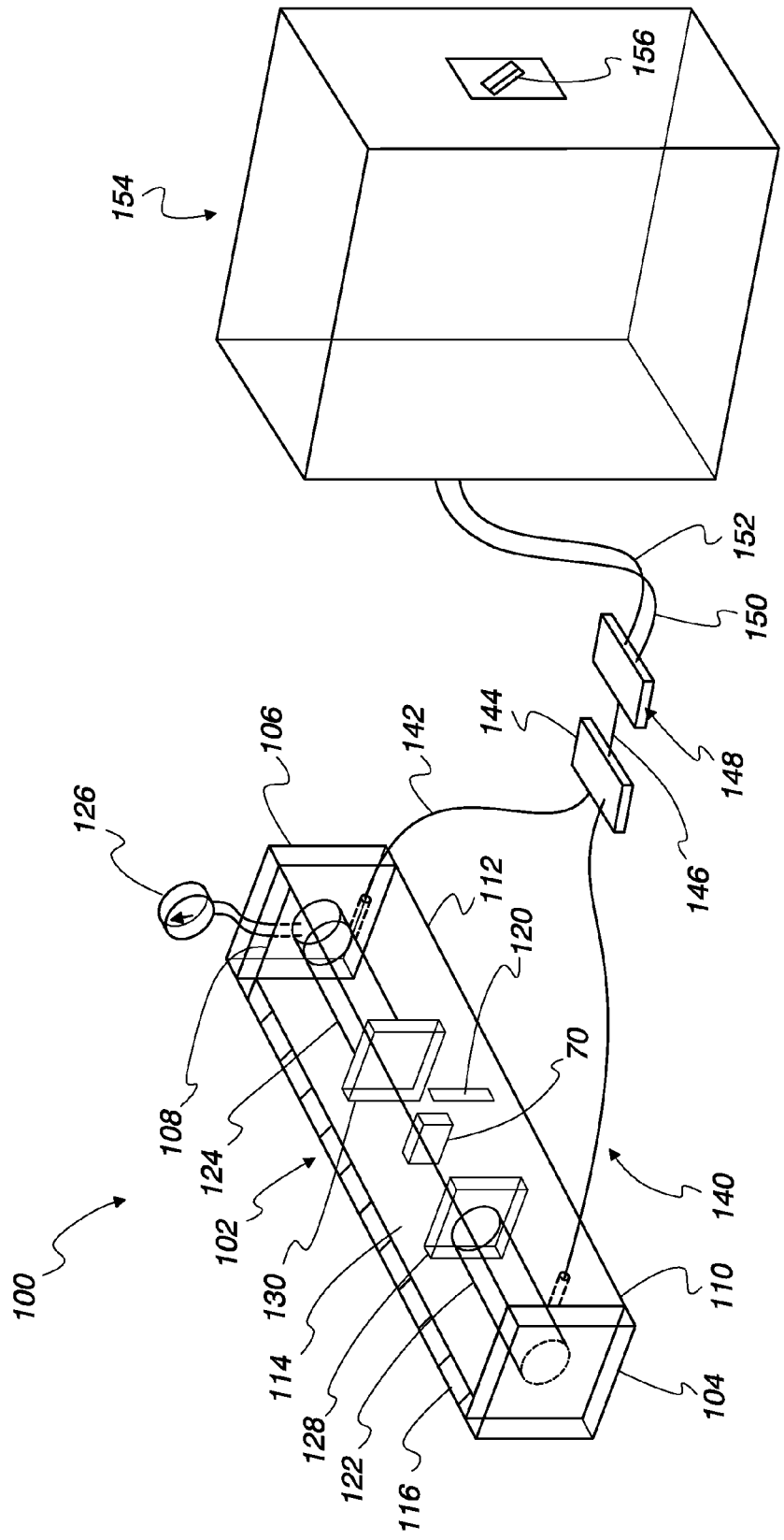
FIG. 7 shows a schematic perspective view of a second exemplary embodiment of an apparatus having two pistons.

FIG. 7 shows an apparatus 100 according to a second exemplary embodiment. The apparatus 100 has a housing 102 that includes end caps 104, 106 and top 108, bottom 110, front 112 and rear 114. A hinge 116 permits the top 108 to pivot to permit access to the interior of the apparatus 100. In exemplary embodiments, the housing 102 may be constructed of high welded high strength steel plate and may be covered with rigid insulation. A sample port 120 may be defined within the front 112 (or may be positioned at another location in the housing 102). A first ram 122 is associated with end cap 104 and a second ram 124 is associated with end cap 106. In exemplary embodiments the rams 122, 124 may be hydraulic rams. In exemplary embodiments the rams 122, 124 may be in a range of 10-20 tons. A gauge 126 is associated with one of the rams, such as ram 124. The gauge 126 may also be associated with the housing 102. A thermal block 128 is mounted at the distal end of the ram 122. Similarly, a thermal block 130 is mounted at the distal end of the ram 124.

The ram 122 is connected to a hydraulic line 140 and the ram 124 is connected to a line 142. The hydraulic lines 140 and 142 are connected to a splitter 144. A line 146 connects the splitter 144 to a pressure limiter 148. A line 150 and a line 152 connect the pressure limiter 148 to a pump system, such as hydraulic pump system 154, which is actuated by a switch 156. A sample 15 in a sample container 70 may be inserted through the port 120 and into the apparatus 100 so as to be positioned between the two thermal blocks 128, 130.

Figure 8:
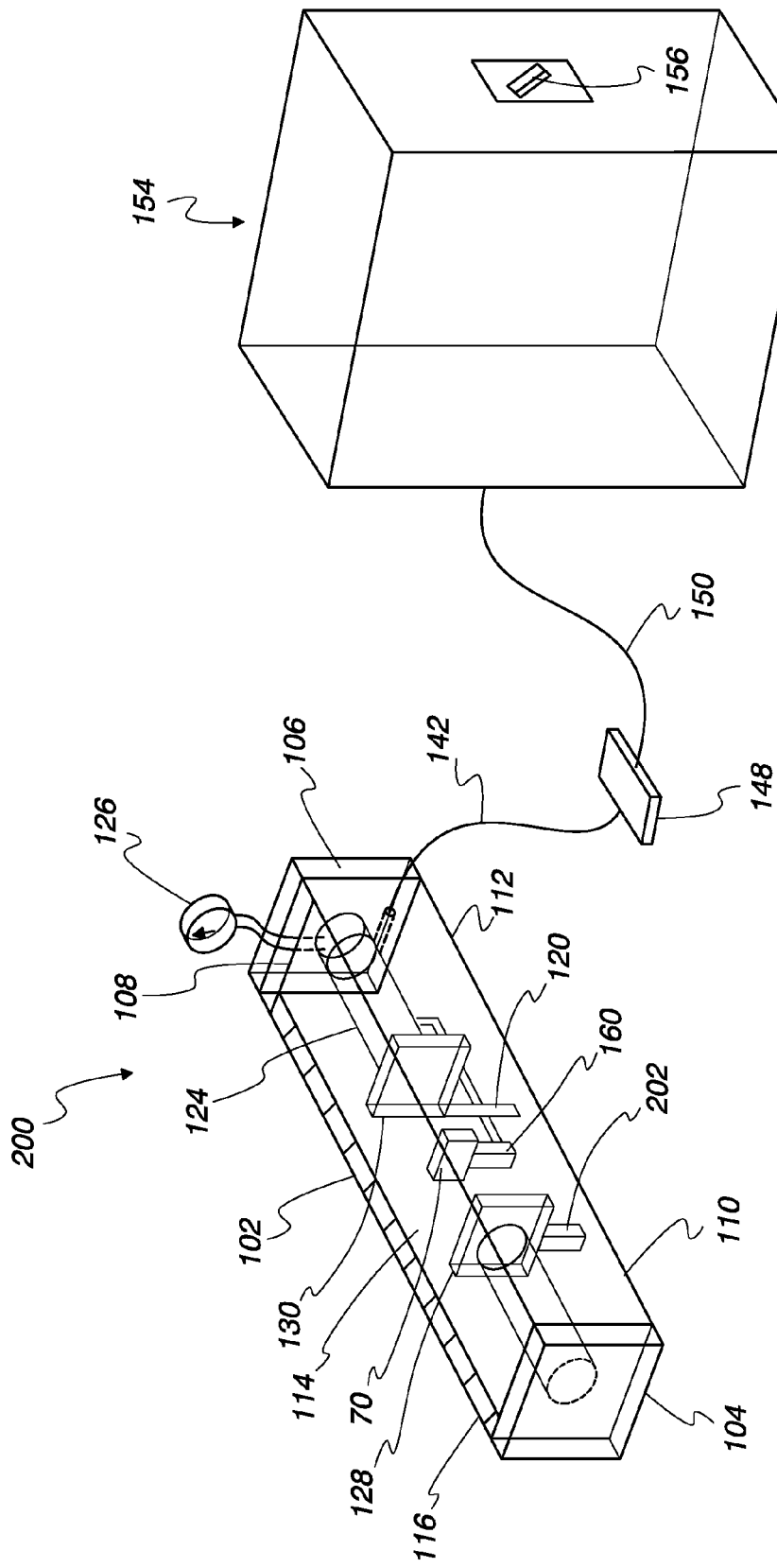
FIG. 8 shows a schematic perspective view of a third exemplary embodiment of an apparatus having one piston.

FIG. 8 shows an apparatus 200 in a third exemplary embodiment. Apparatus 200 is similar to apparatus 100, but the first thermal block is fixed at the distal end of a post 202, and no line 150 or splitter 144 are needed. In this embodiment, the thermal block 130 reciprocatingly moves toward and away from the thermal block 128. In this embodiment the sample 15 (between the sheet 72, 74) moves proportionately with the upper thermal block 20 via mechanical or pneumatic linkage 160 (that is associated with the ram 124) to ensure that the upper and lower blocks 20, 22 contact the sample 15 (via the sheets 72, 74) simultaneously or nearly simultaneously.

High pressure during cooling is known to reduce ice formation in tissues, but can also cause structural or other damage to tissues. High concentrations of cryoprotectant chemicals are also known to reduce ice formation in tissues, but can cause cytotoxic effects and structural damage to cells and tissues. Using the apparatus and methods as disclosed herein, the cooling and warming protocols are designed so that a careful optimal balance of these effects may be achieved so that the risk of deleterious ice formation is eliminated or substantially reduced. In particular, given the thermal characteristics and thickness of the sample 15, the expected maximal cooling and warming rates in the device can be predicted. These cooling and warming rates along with known pressure tolerances of the sample can be used to calculate, using known theories of ice crystallization kinetics, the requisite concentration of CPA that will need to be equilibrated in the sample 15 before the cooling protocol may commence. For example, consider a hypothetical tissue of size 2 mm×10 mm×10 mm with similar heat transfer parameters as human ovarian tissue. Simulations indicate that cooling and warming rates at the center of the tissue are approximately 1000° C./min. Suppose also, that this tissue is mechanically fragile and cannot withstand more than a few atmospheres of pressure. These results may, then, be used in conjunction with published critical cooling and warming rates for cryoprotectants at different concentrations (see, e.g., P. Boutron and P. Mehl. Theoretical prediction of devitrification tendency: Determination of critical warming rates without using finite expansions. Cryobiology, 27:359-377, 1990.) to note that a 40% (w/w) solution of levo-2,3-Butanediol has no ice crystallization at these cooling and warming rates. The predicted successful protocol, then, would be one that facilitates safe equilibration of the hypothetical tissue with the CPA solution before placement in an apparatus as described herein in exemplary embodiments, with the press(es) set to the minimal working pressure needed to maximize sample-to-container and container-to-thermal block contact.

The exemplary embodiments of methods and apparatus disclosed herein may maximize heat transfer coefficients by using liquid-free cryopreservation protocols and maximize glass transition characteristics through increasing pressure during cryopreservation. In particular, it is known that ice nucleation suppression is proportionate to pressure. At high enough pressures, very low cooling rates may be used to achieve vitrification of the sample. Therefore, there is a balance (a phase diagram can be created, in fact) that relates the melting point of solutions with concentration and pressure and then ice crystallization theory can be used to predict the critical cooling and warming rates needed to have "ice-free" or vitrified samples.

In conventional cold-block cooling apparatus, samples are typically not sealed in a container that is fluid-tight sealed for long-term storage. A fluid-tight sample container is a desirable feature because if this is not achieved, tissues must be manipulated into a long-term storage container under liquid nitrogen. The design of the apparatus disclosed herein in exemplary embodiments and the container 70 disclosed herein incorporates the sealing as a feature that facilitates rapid cooling and warming of the sample.

Conventional cold-block apparatus also do not typically cool/warm from two sides simultaneously. This is a desirable feature for tissue cryopreservation because cooling and warming rates are a function of the distance from the cold/heat "source."

Conventional cold-block apparatus also do not utilize pressure as an additional cryoprotective action. This is a desirable feature because the application of pressure allows for potential reduction of required cryoprotective agents that may be cytotoxic, may induce mechanical stresses, or that may require time consuming equilibration protocols. In particular, tissues that are equilibrated with the high concentrations of cryoprotective agent solutions needed to ensure the absence of ice formation during cooling require hours-long protocols before and after the freezing, thawing, and storage of the tissue. Reduced cryoprotectant concentration requirements concomitantly can reduce processing times.

Present cold-block apparatus also do not account for the necessary rapid warming of the tissues before use. It has been shown that this warming rate may even be more critical than the cooling rate. A feature of the presently disclosed apparatus is that the metal (or other thermally conductive materiel) construction of the container results in the tissue already being prepared for ultrarapid warming. This may occur in either a standard warmed water-bath, which would again benefit from the improved heat transfer properties of the liquid free sealed system or rapid warming may be achieved in the apparatus, with the change that the thermal blocks of the apparatus be pre-warmed and/or actively warmed by circulating heating fluids and/or resistive heating instead. This may facilitate even more rapid warming than with many presently available apparatus as the heat transfer characteristics of metal-to-metal are superior to those of water-to-metal.

In exemplary embodiments, the apparatus and methods disclosed herein may be usable in tissue banks for tissue preservation, in hospitals for rapid processing and storage of tissues for later histopathological testing, in agricultural and scientific breeding programs through preservation of reproductive cells and/or tissues), and in other applications. In exemplary embodiments, the methods disclosed herein may be used with custom designed microcontainers to preserve individual cells or small quantities of cells in suspension. The method is simple, allows for robust fluid-tight sealing if needed, and, can facilitate ultrarapid cooling and warming rates for thick tissues that may make possible cryopreservation of many different tissue types.

A feature of the high pressure portion of exemplary embodiments of the apparatus disclosed herein is to maximize sample-to-metal contact, further enhancing heat transfer characteristics. A feature of exemplary embodiments of the present apparatus is the use of two-sided cooling by the thermal blocks 20, 22 or as shown with apparatus 100. Another feature is the high variable (controllable) pressure cooling in the absence of sample-to-liquid heat transfer. Another feature of exemplary embodiments of the disclosed container 70 is that it provides an integrated sample preparation and containment system. A feature of exemplary embodiments of the present methods are the ability to ultrarapidly warm a sample (whereas cryomicroscopy techniques, in comparison, are generally designed for cooling only).

In one exemplary embodiment of a warming method, a sample may be placed directly in a water bath directly from liquid nitrogen (LN). One feature of exemplary embodiments of the presently disclosed apparatus with respect to sample warming is that the pressure may reduce the likelihood of "devitrification," which is the transition from an ice-crystal free glassy state to a crystalline state, generally considered lethal to cells and tissues. One feature of exemplary embodiments of the presently disclosed apparatus and methods may be that, in contrast to traditional rapid cooling, there may be little or no Leidenfrost effect, which may provide improved heat transfer.

In exemplary embodiments, with the appropriate sample dish design, such as one in which there is no air bubble between the media in the sample holder and the top being crimped on to it, cells in suspension (e.g., sperm, oocytes or stem cells in suspension) may be cryopreserved the same way. The thermal characteristics of water (media) vs tissue may make it a bit slower, but still over about $10^4$ K/min.

The following numbered clauses include embodiments that are contemplated and non-limiting.

Clause 1. An apparatus for cryogenically cooling and warming a sample of tissue or cellular material, the apparatus comprising:
  a. a first thermal block having a male sealing member extending therefrom;
  b. a second thermal block having a female sealing member formed therein matable with the male sealing member;
  c. a first force applying means for applying a force to the first thermal block so as to move the first thermal block and the second thermal block into proximity; and,
  d. a chamber for holding the sample, the chamber defined by the first and second thermal blocks and the male sealing member and the female sealing member when the male sealing member is either proximate to or received by the female sealing member.

Clause 2. The apparatus of Clause 1, further comprising a second force applying means for applying a force to the second thermal block.

Clause 3. The apparatus of Clause 2, wherein the first and second forces are adapted to move the first and second thermal blocks toward each other simultaneously.

Clause 4. The apparatus of Clause 1, wherein the first thermal block has a first platen portion wherein the male sealing member substantially surrounds a portion of the first platen portion, and the second thermal block has a second platen portion wherein the female sealing member substantially surrounds a portion of the second platen portion.

Clause 5. The apparatus of Clause 4, wherein the first and second platen portions each have at least a portion having a radius of curvature.

Clause 6. The apparatus of Clause 4, wherein the first and second platens are adapted to move toward each other so as to contact a top surface and a bottom surface of the sample container simultaneously.

Clause 7. The apparatus of Clause 1, wherein the male sealing member comprises a rim.

Clause 8. The apparatus of Clause 1, wherein the female sealing member comprises a groove adapted to receive the male sealing member.

Clause 9. The apparatus of Clause 1, further comprising a sample container adapted to form a fluid-tight sealed container when placed between the first and second thermal blocks and the male and female sealing members engage each other.

Clause 10. The apparatus of Clause 9, wherein the sample container comprises at least two sheets each composed of a thermally conductive material.

Clause 11. The apparatus of Clause 10, wherein the thermally conductive material is crimpable.

Clause 12. The apparatus of Clause 1, further comprising temperature regulating means for cooling or warming at least a portion of the first and second thermal blocks.

Clause 13. The apparatus of Clause 12, wherein the temperature regulating means comprises either at least one liquid, at least one gas or the combination of at least one gas and at least one liquid.

Clause 14. The apparatus of Clause 1, wherein the first force applying means comprises a piston having a first end associated with the first thermal block.

Clause 15. The apparatus of Clause 1, wherein the first force applying means includes a hydraulic pumping system.

Clause 16. The apparatus of Clause 1, further comprising a second force applying means associated with the second thermal block.

Clause 17. A method of cryopreserving a sample of tissue or cellular material, comprising:
  a. placing the sample between at least two sheets of thermally conductive material;
  b. providing a first thermal block having a male sealing member and providing a second thermal block having a female sealing member;
  c. urging the first and second blocks toward each other under pressure so that that the sample and at least a portion of the at least two sheets are contacted between the first and second sealing members so that the first and second sealing members crimp a portion of each sheet to form a fluid-tight sealed chamber having the sample disposed therein;
  d. cooling at least a portion of the first and second thermal blocks to a desired temperature at a desired rate of cooling;
  e. separating the first and second blocks; and,
  f. removing the sample in the container.

Clause 18. The method of Clause 17, wherein the first and second blocks contact the sheets simultaneously.

Clause 19. A method of warming a cryopreserved sample of tissue or cellular material in a container formed according to the method Clause 17, the method comprising:
  a. placing the sample in the container between the first and second thermal blocks;
  b. urging the first and second thermal blocks toward each other such that the first and second thermal blocks contact top and bottom surfaces of the container at generally the same time; and,
  c. warming at least a portion of the first and second thermal blocks so as to warm the sample in the container to a desired temperature at a desired rate of warming.

Clause 20. The method of Clause 19, wherein the sample is placed in a heat conducting fluid prior to being sealed in the container.

Clause 21. The method of Clause 20, wherein the heat conducting liquid is at least one material selected from the group consisting of thermal pasts, greases, mineral oils, and inert mineral oils containing diamond nanoparticles.

EXAMPLES

The examples are provided for illustrative purposes and are not intended to limit the scope of the disclosure. Parts and percentages appearing in such examples are by weight unless otherwise stipulated.

Example 1

Figure 9:
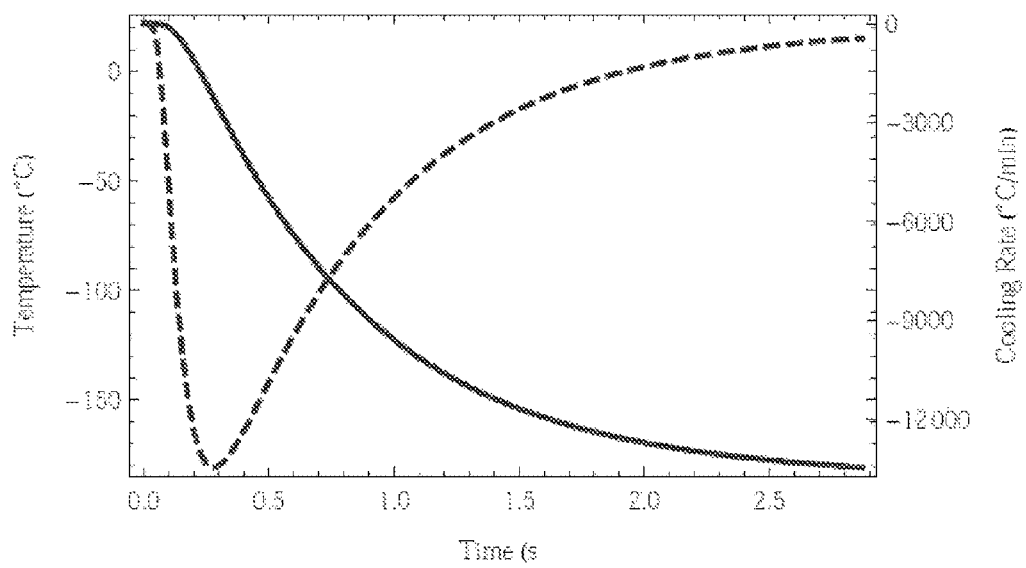
FIG. 9 is a graph of simulated temperature versus time (solid line) and corresponding cooling rate (dashed line) at the center of a 1 mm thick by 10 mm wide tissue.

FIG. 9 is a graph of simulated temperature versus time (solid line) and corresponding cooling rate (dashed line) at the center of a 1 mm thick by 10 mm wide tissue. Aluminum cooled to liquid nitrogen temperatures is used for the block material and the tissue is assumed to be at room temperature. Critically, maximal cooling rates occur while the tissue is most susceptible to damaging ice formation (between 0 and −80° C.). These ~$10^{5°}$ C./min cooling rates combined with 10-100 megapascal pressures dramatically reduces the required concentration of cryoprotective agents (CPAs) needed for ice-free tissue cryopreservation.

Example 2

Figure 10:
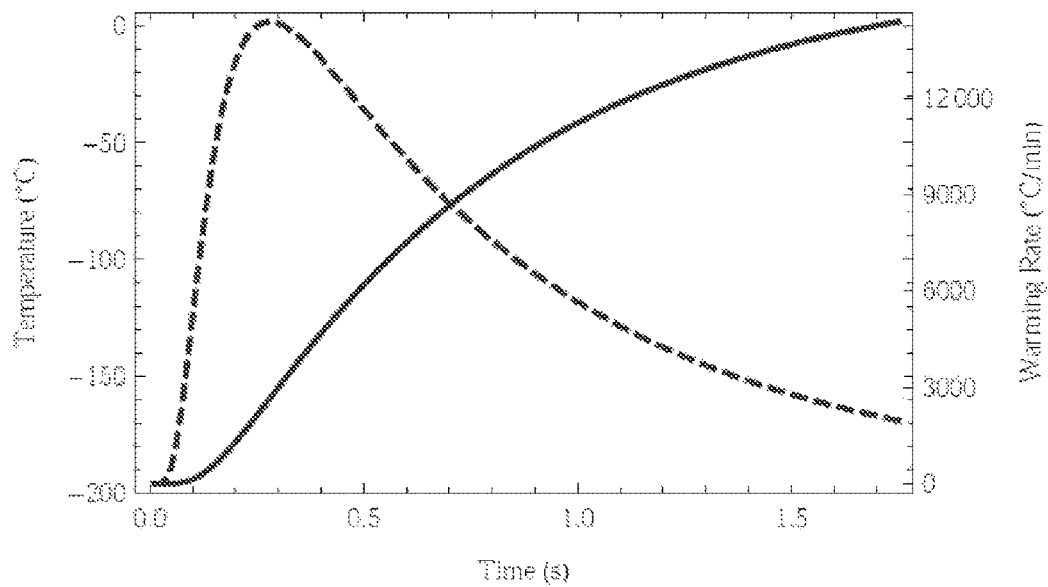
FIG. 10 is a graph of simulated temperature versus time (solid line) and corresponding warming rate (dashed line) at the center of a 1 mm thick by 10 mm wide tissue. Aluminum at room temperatures is used for the block material and the tissue is assumed to be at liquid nitrogen (storage) temperature.

FIG. 10 is a graph of simulated temperature versus time (solid line) and corresponding warming rate (dashed line) at the center of a 1 mm thick by 10 mm wide tissue. Aluminum at room temperatures was used for the block material and the tissue was assumed to be at liquid nitrogen (storage) temperature.

Example 3

Figure 11:
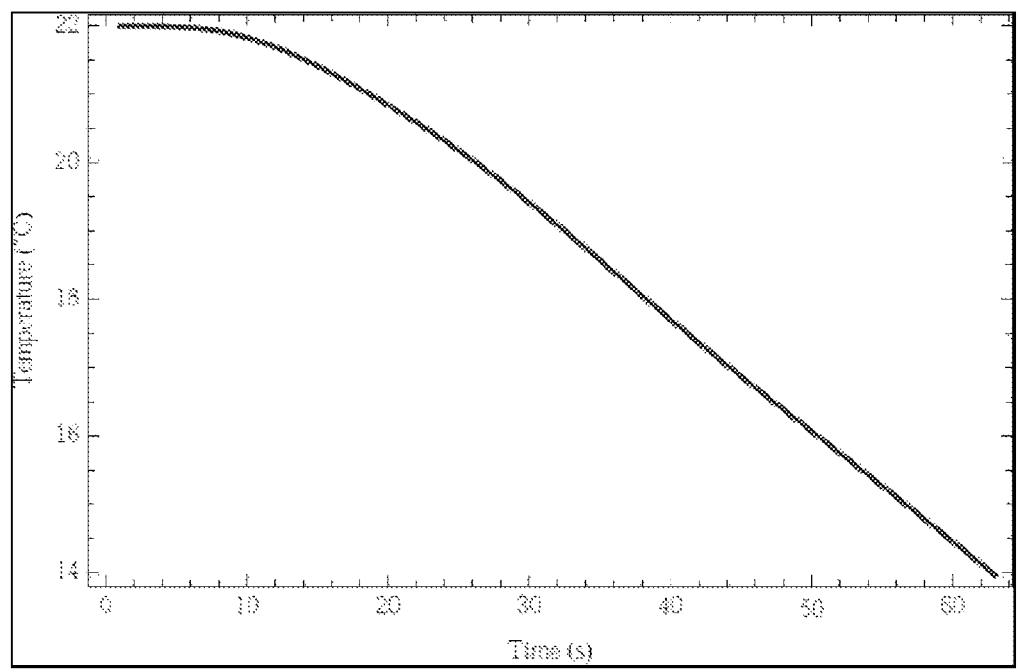
FIG. 11 is a graph of simulated average temperature versus time for a 1 mm thick by 10 mm wide tissue held between two cooling blocks in the open position held 2 cm above and below the sample. This gives an idea of the "working time" to begin the pressing. It is desirable that the temperature not decrease below the freezing point of the material before pressing.

FIG. 11 is a graph of simulated average temperature versus time for a 1 mm thick by 10 mm wide tissue held between two cooling blocks in the open position (see FIG. 1 and FIG. 2) held 2 cm above and below the sample. This gives an idea of the "working time" to begin the pressing. In exemplary embodiments, it is desirable that the temperature remain above the freezing point of the material before pressing.

Prediction Protocol:

1. Using tissue dimensions and tissue-median (e.g., center of tissue), the cooling rates in the apparatus are predicted using software simulations.

2. The resulting thermal profile of the tissue is used in conjunction with known glass transition phase diagrams for common cryoprotectant agents (CPAs) to choose the lowest combination of CPA concentration and allowable pressure that will ensure cooling to liquid nitrogen (LN) temperatures in the absence of the crystallization of water in the sample.

3. The choice of CPA, concentration, and pressure will depend on tissue specific parameters such as CPA toxicity, sensitivity to pressure, among others.

4. Given tissue dimensions, simulations will be performed to determine optimal CPA exposure time, protocol, and or temperature to ensure adequate but safe equilibration throughout the tissue.

Cooling Protocol:

1. A sample of 1 mm thickness is exposed to tissue culture media containing a predicted optimal amount of CPA for a predicted required length of time at a specified temperature.

2. The sample is removed from the media, gently wiped dry with sterile tissue, placed in bottom half of a sample container, and mounted in place in the apparatus (between upper and lower blocks—blocks are sufficient distance away that sample is not cooled below crystallization temperature of sample).

3. While samples are being processed, the aluminum thermal blocks are equilibrated in liquid nitrogen (LN).

4. When the sample is in the container and is ready to be cryopreserved, the thermal blocks are placed in the press or proximate to the press mechanism or mechanisms.

5. The press is immediately activated at the predetermined pressure.

6. The action of the press simultaneously or nearly simultaneously (a) presses the top of the sample container tightly to the top of the sample, (b) presses the top thermal block on the top of the sample and the sample tightly on the bottom thermal block, and (c) crimps the sides of the sample container together.

7. The press is held closed for 5 seconds, or long enough so that the sample is in thermal equilibrium with the blocks.

8. The thermal blocks are removed while held together and placed in LN (or the whole system is submerged in LN).

9. Once the sample and the thermal blocks are bathed in LN, the thermal blocks are separated and the container containing the sample is removed and transferred to long term storage.

Warming Protocol:

1. The thermal blocks are pre-equilibrated in a 37° C. water bath (or other appropriate physiologic temperature).

2. The sample in its container is removed from storage and immediately placed in the apparatus sample holder.

3. The press is activated at the predetermined pressure.

4. The action of the press simultaneously or nearly simultaneously (a) presses the top of the sample container tightly to the top of the sample, (b) presses the top thermal block on the top of the sample and the sample tightly on the bottom thermal block, and (c) crimps the sides of the sample container together.

5. The press is closed for 5 seconds or long enough so that the sample is in thermal equilibrium with the blocks.

6. The press is opened, the sample container removed and opened, and the tissue is ready for use.

The invention claimed is:

1. An apparatus for cryogenically cooling and warming a sample of tissue or cellular material, the apparatus comprising:
   a) a first thermal block having a means associated therewith for pre-cooling at least a portion of the first thermal block, and having a male sealing member extending therefrom;
   b) a second thermal block having a means associated therewith for pre-cooling at least a portion of the second thermal block, and having a female sealing member formed therein matable with the male sealing member;
   c) a support for suspending the sample between the first thermal block and second thermal block;
   d) a first force applying means for applying a force to the first thermal block so as to move the first thermal block and the second thermal block into proximity; and
   e) a chamber for holding the sample, the chamber defined by the first and second thermal blocks and the male sealing member and the female sealing member when the male sealing member is either proximate to or received by the female sealing member.

2. The apparatus of claim 1, further comprising a second force applying means for applying a force to the second thermal block.

3. The apparatus of claim 2, wherein the first and second force applying means are adapted to move the first and second thermal blocks toward each other simultaneously.

4. The apparatus of claim 1, wherein the first thermal block has a first platen portion wherein the male sealing member substantially surrounds a portion of the first platen portion, and the second thermal block has a second platen portion wherein the female sealing member substantially surrounds a portion of the second platen portion.

5. The apparatus of claim 4, wherein the first and second platen portions each have at least a portion having a radius of curvature.

6. The apparatus of claim 4, wherein the first and second platens are adapted to move toward each other so as to contact a top surface and a bottom surface of the sample container simultaneously, and wherein the first platen portion and second platen portion are pre-cooled prior to movement of the first and second platens towards each other.

7. The apparatus of claim 1, wherein the male sealing member comprises a rim.

8. The apparatus of claim 1, wherein the female sealing member comprises a groove adapted to receive the male sealing member.

9. The apparatus of claim 1, further comprising a sample container adapted to form a fluid-tight sealed container when placed between the first and second thermal blocks and the male and female sealing members engage each other.

10. The apparatus of claim 9, wherein the sample container comprises at least two sheets each composed of a thermally conductive material.

11. The apparatus of claim 10, wherein the thermally conductive material is adapted to crimp.

12. The apparatus of claim 1, further comprising temperature regulating means for cooling or warming at least a portion of the first and second thermal blocks.

13. The apparatus of claim 12, wherein the temperature regulating means comprises either at least one liquid, at least one gas or the combination of at least one gas and at least one liquid.

14. The apparatus of claim 1, wherein the first force applying means comprises a piston having a first end associated with the first thermal block.

15. The apparatus of claim 1, wherein the first force applying means includes a hydraulic pumping system.

16. A method of cryopreserving a sample of tissue or cellular material, comprising:
   a) placing the sample between and in contact with at least two sheets of thermally conductive material;
   b) providing a first thermal block, at least a portion of which being pre-cooled, and having a male sealing member and providing a second thermal block, at least a portion of which being pre-cooled, and having a female sealing member;
   c) urging the first and second blocks toward each other such that that the sample and at least a portion of the at least two sheets are contacted between the first and second sealing members so that the first and second sealing members crimp a portion of each sheet to form a fluid-tight sealed container including a chamber having the sample disposed therein;
   d) cooling at least a portion of the first and second thermal blocks to a desired temperature at a desired rate of cooling;
   e) separating the first and second blocks; and,
   f) removing the sample in the container.

17. The method of claim 16, wherein the first and second blocks contact the sheets simultaneously.

18. A method of warming a cryopreserved sample of tissue or cellular material in a container formed according to the method of claim 16, the method comprising:
   a) placing the sample in the container between the first and second thermal blocks;
   b) urging the first and second thermal blocks toward each other such that the first and second thermal blocks contact top and bottom surfaces of the container at generally the same time; and,
   c) warming at least a portion of the first and second thermal blocks so as to warm the sample in the container to a desired temperature at a desired rate of warming.

19. A method of warming a cryopreserved sample of tissue or cellular material in a container formed according to the method of claim 16, the method comprising:
   a) placing the sample in the container between the first and second thermal blocks;
   b) contacting the sample with a heat-conducting fluid prior to being sealed in the container;
   c) urging the first and second thermal blocks toward each other such that the first and second thermal blocks contact top and bottom surfaces of the container at generally the same time; and,
   d) warming at least a portion of the first and second thermal blocks so as to warm the sample in the container to a desired temperature at a desired rate of warming.

20. The method of claim 19, wherein the heat conducting fluid is at least one material selected from the group consisting of thermal pastes, greases, mineral oils, and inert mineral oils containing diamond nanoparticles.

* * * * *